United States Patent
Schubert

(10) Patent No.: US 6,649,165 B2
(45) Date of Patent: Nov. 18, 2003

(54) METHOD OF BLOCKING CYTOTOXIC ACTIVITY IN PATIENTS WITH AMYOTROPHIC LATERAL SCLEROSIS USING SOLUBLE FCγRIII RECEPTORS

(76) Inventor: Walter Schubert, Am Muhlengrund 9, D-39175 Biederitz (DE)

(*) Notice: Subject to any disclaimer, the term of this patent is extended or adjusted under 35 U.S.C. 154(b) by 70 days.

(21) Appl. No.: 09/802,305

(22) Filed: Mar. 8, 2001

(65) Prior Publication Data

US 2001/0055592 A1 Dec. 27, 2001

Related U.S. Application Data

(62) Division of application No. 09/367,011, filed as application No. PCT/DE97/02883 on Dec. 10, 1997.

(51) Int. Cl.[7] ............ A61K 38/17; C07K 14/705; C07K 14/735
(52) U.S. Cl. ............ 424/184.1; 424/810; 514/2; 514/8; 514/885; 530/350; 530/868
(58) Field of Search ............... 530/350, 868; 424/184.1, 810; 514/885, 2, 8

(56) References Cited

FOREIGN PATENT DOCUMENTS

DE 197 23 690 A 3/1998

OTHER PUBLICATIONS

Schubert, et al., "Detection by 4–parameter microscopic imaging and increase of rare mononuclear blood leukocyte types expressing . . . " NEUROSCIENCE LETTERS, vol. 198, No. 1, Sep. 22, 1995.
Kahan Cur. Opin. Immunol. 4:553–560 1992.
Tan et al. Arch Neurol. 51:194–200 1994.
Dalakas et al. Arch Neurol. 51:861–864 1994.
Ludolph J. Neurol. 247:13–18 2000.
Serratrice et al. Adv. Neurol 68:1–5 1995.

*Primary Examiner*—Phillip Gambel
*Assistant Examiner*—Jessica H. Roark
(74) *Attorney, Agent, or Firm*—Weingarten, Schurgin, Gagnebin & Lebovici LLP

(57) ABSTRACT

The present invention is directed to a method of blocking the cytotoxic activity of FcγRIII receptor-positive immune cells in a patient with amyotrophic lateral sclerosis using an effective amount of soluble FcγRIII receptors. The soluble FcγRIII receptors of the invention are specific for immunoglobulin G of under-class 1 (IgG1) and/or 3 (IgG3).

7 Claims, No Drawings

METHOD OF BLOCKING CYTOTOXIC ACTIVITY IN PATIENTS WITH AMYOTROPHIC LATERAL SCLEROSIS USING SOLUBLE FCγRIII RECEPTORS

CROSS-REFERENCE TO RELATED APPLICATIONS

This application is a divisional of Application No. 09/367,011 filed Sep. 7, 1999, which is a National Stage of International Applicatioon No. PCT/DE97/02883, filed Dec. 10, 1997, the whole of which is hereby incorporated by reference herein.

FIELD OF THE INVENTION

The invention relates to the use of substances having a well-directed, i.e. selective, effect on a certain receptor family (FcγR) or on those immune system cells with defined surface characteristics which express said receptor and whose presence—in examinations performed by the applicant—has been found to be specific, or its number specifically increased, in the case of amyotrophic lateral sclerosis.

BACKGROUND OF THE INVENTION

Amyotrophic lateral sclerosis (in the following referred to as ALS, its abbreviation) is a neurodegenerative disease of the human motoneuron system which usually takes a lethal course within 3 to 5 years, whose causes have not been determined etiologically and for which there is no, or no significant, therapy as yet. The progressive decay of nerve cells of the first and second motor neurons are the cause of an increasing paralysis of the voluntary muscles, eventually leading to a total walking inability and the increasing paralysis of the respiratory musculature. It has largely been proven that cellular and humoral (antibody-mediated) immunological processes play an important role, if yet unexplained in the individual case, in the pathogenesis of ALS. Worldwide, the prevalence of this disease is 4 in 100,000 and its incidence is 1 in 100,000 inhabitants.

Numerous examination results seem to imply that immunological mechanisms are at play in the pathogenesis of amyotrophic lateral sclerosis. The following findings substantiate this assumption: Cytotoxic serum activity of ALS patients in neuronal cell cultures; serum immunoglobulin G (IgG) toxicity against spinal and cortical neurons as well as voltage-dependent calcium channel proteins; cytotoxicity of the cerebrospinal fluid of ALS patients against glutamate receptors; changes of the serum concentration of IgG isotypes; immune response of peripheral blood lymphocytes of ALS patients to isolated cell membranes; detection of invasive immune system cells in the motoneuron system of ALS patients. Here, these cells seem to be involved in the motoneuron damaging mechanisms (the quotations of the individual above data can be found in: Westarp, M. E. et al., Neurosci. Lett. 173, 124–126, 1994).

Although this data seems to imply a probable involvement of the cellular immune system in ALS, it has been impossible so far to detect definite quantitative or qualitative changes in the cellular immune system in the case of ALS. In particular, no ALS specific cell types have so far been found in the blood of ALS patients which would be identifiable by their molecular cell surface characteristics and clearly differ from immune cells of healthy experimentees or present in other neurological diseases. Nevertheless, countless therapies involving medication with a relatively broad effectivity as well as an undirected action were attempted in order to suppress or at least modulate immune functions. However, any such therapy attempt has remained without ascertained therapeutical success (cf. e.g. Brown, R. H. et al.: Arch. Neurol. 43, 383–384, 1986; and e.g. Dalakas, M. C. et al.: Arch. Neurol. 51, 861–864, 1994). A disadvantage of such approach is that these forms of therapy (blind or unaware of specific cell parameters with ALS) are not well-directed, i.e. they do not block or suppress exclusively those cell types which are specifically present, or present in significantly increased numbers, in ALS patients.

Tests performed by the applicant have shown that the blood of ALS patients contains mononucleic cells of the immune system which are not found with any other neurological disease or in healthy persons (ALS specific immune cells, cf. Table 1). Contrary to the immune cell types so far observed to be present in increased numbers in ALS patients which are known as prior art (Schubert, W.; Neurosci. Lett. 198, 29–32, 1995), the cell types discovered according to the invention and listed in Table 1 are totally ALS specific. These cell types express receptors for immunoglobulins (Fcγ receptors), preferably for immunoglobulin G (IgG) of underclass 1 (IgG1) and 3 (IgG3) (in the following referred to as FcγRIII). The increased number, or the ALS specific occurrence, of said immune cells is an explanation of the hitherto unexplained reduction of IgG1 and IgG3 in the serum of patients diagnosed with ALS which was reported e.g. by Westarp et al. (Westarp, M. E. et al., Neurosci. Lett. 173, 124–126, 1994): FcγRIII receptors selectively bind to these immunoglobulins, i.e. a multiplication of cells expressing said receptors (as discovered in applicant's own studies) will result in increased binding to IgG1 and IgG3 and thus an IgG1–IgG3 clearance in this disease. In applicant's own studies, it has been found for the first time that these Fcγ receptor-positive cells exhibit a series of molecular activation characteristics on the cellular surface and, when cultured, will cause damage to, or even the destruction of, nerve cells. These cells are therefore directly involved in the pathomechanism of ALS and, as a cellular form, for the first time constitute a concrete target structure for a well-directed, i.e. specific, therapy with immunoactive substances.

The present invention is therefore based on the discovery of Fcγ receptor positive, in particular FcγRIII positive, activated cellular forms in the blood stream which are ALS specific, or significantly increased in number in the case of ALS, and relates to a use of substances for the selective suppression, destruction or selective functional blocking of said cellular forms, or blocking or functional inactivation of Fcγ receptors, by infusion or injection of defined substances as specified in claim 1.

Fcγ receptors have been known for quite some time in immunology. There are three different, yet related classes of human Fcγ receptors: FcγRI, FcγRII and FcγRIII. The amino acid sequences of the members of this receptor family as well as the genes coding for said receptors are known: FcγRI (Allen, J. M., Seed B.: Science 243, 378–380, 1989), FcγRII (Ravetch, J. V., Kinet, J.-P.: Annu. Rev. Immunol. 9, 457–492, 1991), FcγRIII (Ravetch, J. V., Perussia, B.: J. Exp. Med. 170, 481–497, 1989). Most subtypes of these three receptor classes are anchored in the cell membrane of certain immune cells. However, all three classes also contain soluble receptor proteins, i.e. proteins not anchored in the cell membrane, which are naturally released by immune cells. The mechanisms are different, however. Soluble FcγRI receptors are generated by a stop codon in the extracellular domain. Soluble FcγRII receptors are generated by alternative RNA splicing, and soluble FcγRIII receptors are generated by proteolytic splitting of the receptor anchored in the cell membrane (cf. summarizing survey in: Jan, G. J. et al.: Immunology Today, 14, 215–221, 1993).

Said Fcγ receptors are particularly relevant for a number of important immunologic functions. All these functions are based on the fact that Fcγ receptors specifically bind to G immunoglobulins. The binding of such immunoglobulins to Fcγ receptors stimulates or triggers a variety of different cellular activities: Phagocytosis, endocytosis, antibody-dependent cell-mediated cytotoxicity, the release of soluble, inflammation-promoting factors (mediators) as well as the increase of antigen presenting mechanisms. G immunoglobulins bind to Fcγ receptors via their Fc parts If G immunoglobulins for example bind to Fcγ receptors anchored on the surface of certain immune cells in this manner, said immune cells will then be capable of binding very specifically to antigen-bearing target cells and destroying them. These mechanisms probably play an important pathogenetic part in numerous socalled autoimmune diseases. In some cases it has been possible to show that blocking or functionally inactivating said mechanisms largely prevents the disease-specific destruction of target cells. One example hereof is a rare form of an autoimmune disease in humans, the socalled acute immuno-thrombocytopenic purpura, in which an Fcγ receptor-mediated cytotoxic activity of the immune system against blood platelets results in an acute diminution of said platelets (thrombocytes) in the blood of affected patients. In this case, it has been possible to show that the infusion of soluble Fcγ receptor fragments results in a clear recovery from the symptoms and the cellular signs of the disease (Debré et al.: Lancet, 342, 945–948, 1993).

In the case of ALS, however, an immunological pathomechanism based on the activity of Fcγ receptors has not been known so far. Also, a form of therapy directed at specifically inactivating or blocking such mechanism has not been developed or conducted.

Now, however, the existence of accordingly specific cellular forms and such mechanisms has been confirmed by the results of examinations conducted by the applicant.

In detail, it has been found that the blood of ALS patients contains mononucleic cells bearing Fcγ receptors on their cellular surfaces, additionally or simultaneously bearing a different number of various other receptor proteins which exhibit an unusual form of cellular surface activation. The surface receptors variably co-expressed together with Fcγ receptors, above all FcγRIII receptors, are individually designated in Table 1. The abbreviations (CD) used therein are in keeping with the international nomenclature (cf. Barcley, A. N. et al.: The leucocyte antigen facts book. Academic press. London. 1993). This special combination of Fcγ receptors (e.g. CD16) with other receptor proteins indicated in Table 1 is ALS specific since it could not be detected in healthy persons or with other neurological control diseases or other immunological, non-neurological diseases;

that these cells, after being isolated from the blood of ALS patients, could be cultivated in cell culture media (the standard protocols on which this was based are described in Lindl, T., Bauer, J.: Zell- und Gewebekultur, published by G. Fischer Verlag, Stuttgart, 1987), that said cells, after enrichment and in co-cultivation with nerve cells and serum of ALS patients, develop a cytotoxic activity resulting in the destruction of the nerve cells, that it is possible to block said cytotoxic activity by the addition of various soluble factors:
  a) by monoclonal antibodies against Fcγ receptors at a concentration of between 20 and 100 μmol,
  b) by soluble Fcγ receptors at a concentration of between 10 and 60 μmol,
  c) by anti-sense messenger ribonucleic acid species (mRNA) which are complementary to Fcγ receptor-specific mRNA sequences (e.g. 20 μmol of a no. 23 anti-sense oligonucleotide, derived from EMBL/gene bank FcγRIII sequence X16863),
  d) by protein V isolated from *Gardnerella vaginalis* (EP: 0595997) at concentrations of between 150 to 170 μmol in the simultaneous presence of serum from ALS patients.

Consequently, the solution according to the invention is the blocking of the Fcγ receptor-mediated cytotoxic activity of the ALS-specific Fcγ receptor-positive immune cells, or the blocking or the inactivation of Fcγ receptors, or the destruction thereof, by the administration of the abovementioned substances, so as to prevent the direct or indirect pathological effects of these cells or the Fcγ receptors on the motoneuron system.

Said substances will therefore be applied in the respective therapeutic dosage and after a toleration test in bolus (see the examples). Approximate values are the following concentrations, for example: for FcγR specific antibodies (10 to 1,000 mg/weight kg, once or twice a day i.v.), for Fcγ receptor specific anti-sense RNA (10 to 20 mg/kg), for soluble Fcγ receptors (10 to 1,000 mg/kg), for protein V (10 to 1,000 mg/kg).

However, an exact therapeutic dose can only be decided on with respect to the individual case concerned. It depends, amongst other things, on the response of the Fcγ receptor-positive cells to the administration of the substances as indicated in claim 1 and on the individual toleration which may be determined by single bolus administrations (see example 1). Such response may e.g. be established by the determination of the number of such cellular forms in the blood or by in-vitro cytotoxicity assays. If necessary, the dosage and the distribution of the daily dosis may have to be modified according to the individual case concerned.

The solution according to the invention has the following advantages:

1. In contrast to all other forms of immunosuppressive or immunomodulating therapy performed so far which were substantially unspecific and affected the entire immune system, the form of therapy disclosed herein constitutes a well-directed form of therapy, i.e. directed at ALS specific forms of immune cells.
2. Based on the knowledge, according to the invention, of the ALS specific surface characteristics, i.e. the combinatorial receptor patterns of these cells (see Table 1), it is possible to ascertain before each therapy whether these cells are present at all, or, after their isolation and in-vitro testing, to determine whether they exhibit any cytotoxic, in particular neurotoxic, activity.
3. Based on the knowledge, according to the invention, of the cell surface characteristics of these cells, the therapeutical success can not only be determined clinically, but also on a cellular level, with the therapy according to claim 1 in full progress, by the examination of blood samples for a therapy-related decrease in the number, or even a total elimination, of the Fcγ receptor-positive cellular forms from the blood stream.
4. Based on the findings of above step 3, the dosage of the administered substances may be adapted accordingly, i.e. increased or decreased, depending on whether or not there is a response of the Fcγ receptor-positive cellular forms.
5. Since the knowledge, according to the invention, of the cell surface characteristics of the ALS specific cellular forms for the first time constitutes a disease-specific cell parameter for ALS, it is possible to correlate the clinical course of the disease precisely with this parameter so that, even after a discontinuation of the therapy in accordance with the inventive use of Fcγ receptor-specific substances, a potential re-increase of the Fcγ receptor-positive cells will allow exact determination of the time for a further therapy cycle.

EXAMPLES

The solution according to the invention, including the way it works, is described in more detail hereinafter with reference to an embodiment.

Example 1

| | |
|---|---|
| Patient | X1 |
| Diagnosis | ALS, bulbous type |
| Substance | soluble Fcγ receptor preparations, 50 kDa, from *E. coli* (fusion proteins from *E. coli*) |
| Mode of application | intravenous |
| Therapeutical scheme | toleration test with 10 to 1,000 mg/kg in bolus i.v., subsequently 150 mg/weight kg daily, over a period of 5 days |

TABLE 1

| CD | ALS | | | | | | | | | | | | | | | | | Control |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | n |
| CD16 | + | + | + | + | + | + | + | + | + | + | + | + | + | + | + | + | + | + |
| CD2 | + | + | + | + | + | − | − | − | − | − | − | − | − | − | − | − | − | − |
| CD3 | + | + | + | + | + | + | + | + | + | + | + | + | + | + | + | + | + | + |
| CD4 | + | + | + | + | + | + | + | − | + | + | + | + | + | + | + | − | − | + |
| CD8 | − | + | − | − | − | − | − | − | − | − | − | − | − | − | − | − | − | − |
| CD56 | − | − | + | + | + | + | + | + | + | + | + | − | − | − | − | + | + | − |
| CD57 | + | − | + | − | − | − | − | − | − | − | − | − | − | − | − | − | − | − |
| CD26 | − | + | − | − | − | − | − | − | − | − | − | − | − | − | − | − | − | − |
| CD38 | + | − | + | + | + | + | + | + | + | + | + | + | + | + | + | + | + | + |
| CD71 | − | + | − | − | − | − | − | − | − | − | − | − | − | − | − | − | − | − |
| HLA-DR | + | − | + | + | + | + | + | + | + | + | − | + | + | − | − | − | − | − |
| HLA-DQ | − | − | − | − | − | − | − | − | − | − | − | − | − | − | − | − | − | − |
| CD11b | + | − | − | − | − | + | + | − | − | − | − | + | − | + | + | − | − | − |
| CD45Ra | − | + | − | − | − | − | − | − | − | − | − | − | − | − | − | − | − | − |
| CD7 | + | − | + | − | − | + | − | + | − | − | − | − | + | − | − | − | − | − |
| CD62L | + | − | + | + | − | + | + | + | + | − | − | + | + | + | − | − | + | + |
| CD36 | − | + | − | − | − | − | − | − | − | − | − | − | − | − | − | − | − | − |
| CD19 | − | − | − | − | − | − | − | − | − | − | − | − | − | − | − | − | − | − |

CD: "Cluster of differentiation antigens" of mononucleic peripheral blood leucocytes isolated on the cell surface; 1 to 17: different ALS specific cellular forms simultaneously expressing CD16 (FcγRIII) in different combinations with other CD-surface antigens on the cell surface; n: FcγRIII-positive normal immune cellular form in a healthy experimentee

What is claimed is:

1. A method of blocking the cytotoxic activity of FcγRIII receptor-positive immune cells in a patient with amyotrophic lateral sclerosis, said method comprising the step of:
   (a) administering to said patient an effective amount of soluble FcγRIII receptors, wherein said soluble FcγRIII receptors bind to immunoglobulins in said patient to inhibit the cytotoxic activity of FcγRIII receptor-positive immune cells in said patient.

2. A method of claim 1, wherein said immunoglobulins are immunoglobulins G of under-class 1 (IgG1) and/or 3 (IgG3).

3. A method of claim 1, wherein said soluble FcγRIII receptors are administered at a concentration of between 10 and 60 μmol.

4. A method of claim 1, wherein said soluble FcγRIII receptors are administered in an amount of between 10 to 1,000 mg/weight kg.

5. A method of claim 1, wherein said administering is by infusion or injection.

6. A method of claim 1, wherein said soluble FcγRIII receptors bind to IgG1 to block FcγRIII receptor activity.

7. A method of claim 1, wherein said soluble FcγRIII receptors bind to IgG3 to block FcγRIII receptor activity.

* * * * *

UNITED STATES PATENT AND TRADEMARK OFFICE
CERTIFICATE OF CORRECTION

PATENT NO.   : 6,649,165 B2
DATED        : November 18, 2003
INVENTOR(S)  : Walter Schubert Page 1 of 1

It is certified that error appears in the above-identified patent and that said Letters Patent is hereby corrected as shown below:

Title page, Item [54] and Column 1, line 4,
Title, "FCγRIII" should read -- FcγRIII --;

Column 2,
After line 55, insert the following header:
    -- DETAILED DESCRIPTION OF THE INVENTION --;

Column 3,
Line 30, "parts If" should read -- parts. If --.

Signed and Sealed this

Twenty-eighth Day of December, 2004

JON W. DUDAS
*Director of the United States Patent and Trademark Office*